United States Patent [19]
Ryan et al.

[11] Patent Number: 5,196,513
[45] Date of Patent: Mar. 23, 1993

[54] SYNTHETIC PEPTIDES DERIVED FROM THE BETA-SUBUNIT OF HUMAN THYROID STIMULATING HORMONE

[75] Inventors: Robert J. Ryan; Daniel J. McCormick; John C. Morris, all of Rochester, Minn.

[73] Assignee: Mayo Foundation for Medical Education and Research, Rochester, Minn.

[21] Appl. No.: 736,030

[22] Filed: Jul. 25, 1991

Related U.S. Application Data

[63] Continuation of Ser. No. 403,564, Sep. 5, 1989, abandoned.

[51] Int. Cl.$^5$ .............................................. C07K 7/00
[52] U.S. Cl. .................................... 530/327; 530/397; 530/326; 530/398
[58] Field of Search ................ 530/326, 327, 397, 398

[56] References Cited

U.S. PATENT DOCUMENTS 3,941,763  3/1976  Sarantakis ........................... 404/177
4,609,622  9/1986  Kohn et al. ............................ 435/29

OTHER PUBLICATIONS

Carr et al., *J. Biol. Chem.* 262(3): 961–987 (1987).
Croyle et al., *DNA* 5(4): 299–304 (1986).
Hayashizaki et al. *FEBS* 188(2): 394–400 (1985).
Licht, et al., Recent Prog. Horm. Res. 33: 169–248 (1977).
Vaitukaitis, et al., Recent Prog. Horm. Res. 32: 289–331 (1976).
Ward, et al., Recent Prog. Horm. Res. 29: 533–561 (1973).
Papkoff, et al., Recent Prog. Horm. Res. 29: 563–590 (1973).
Canfield, et al., Recent Prog. Horm. Res. 27: 121–164 (1971).
Pierce, et al., Recent Prog. Horm. Res. 27: 165–212 (1971).
Ryan, et al., Recent Prog. Horm. Res. 26, 105–137 (1970).
Pierce, J. C., in *The Thyroid: A Fundamental and Clinical Text*, (Ingbar and Braverman, eds.), pp. 267–271 (5th Ed., J. B. Lippincott, Philadelphia, PA, 1986).
Pierce, J. G. and T. F. Parsons, *Ann. Rev. Biochem.* 50: 465–495 (1981).
Ji, I.l and T. H. Ji, *Proc. Natl. Acad. Sci, U.S.A.* 78: 5465–5469 (1981).
Ascoli M. and D. L. Segaloff, *J. Biol. Chem.* 261: 3807–3815 (1986).
Moudgal, N. R. and C. H. Li, *Proc. Natl. Acad. Sci, U.S.A.* 79: 2500–2503 (1982).
Grasso, P. and T. M. Crisp, *Endocrinology* 116: 319–327 (1985).
Armstrong, et al., *Biochemical Actions of Hormones* 13: 91–128 (1986).
Volpe, R., in *The Thyroid: A Fundamental and Clinical Text*, (Ingbar and Braverman, eds.), pp. 747–767 (5th Ed., J. B. Lippincott, Philadelphia, PA 1986).
Smith, B. R. and P. R. Buckland, *Receptors, Antibodies, and Disease*, (CIBA Foundation Symposium), pp. 114–132 (1982).
Fahraeus-van Ree, G. E. and N. R. Farid, *Clin. Res.* 31: 679A (1983).
Davies, T. F. and M. Platzer, *Clin. Endocrinol.* 19: 427–435 (1983).
Morris, et al., *Endocrinology* 123: 456–462 (1988).
Charlesworth, et al., *J. Biol. Chem.*; 262: 13409–13416 (1987).
Morris et al., *J. Clin. Endocrinol. Metab.* 67: 707–712 (1988).

(List continued on next page.)

Primary Examiner—Garnette D. Draper
Assistant Examiner—Shelly J. Guest
Attorney, Agent, or Firm—Merchant, Gould, Smith, Edell, Welter & Schmidt

[57] ABSTRACT

Synthetic peptides corresponding to β-subunit of human thyroid stimulating hormone amino acid regions β1-15, β81-95, and β101-112, were found to potently inhibit the stimulation of adenylate cyclase activity by bTSH in a TSH bioassay using FRTL$_5$ cells and block the action of thyroid stimulating immunoglobulin.

1 Claim, 8 Drawing Sheets

OTHER PUBLICATIONS

Steward and Young, *Solid Phase Peptide Synthesis* (2d ed.), Pierce Chemical Co., Rockford, Ill., pp. 1-157 (1984).
McCormick, et al., *J. Immunol.* 139: 2615-2619 (1987).
Heinrikson, R. L. and S. C. Meredith, *Anal. Biochem.* 136: 65-74 (1984).
Takahashi, et al., *J. Clin. Endocrinol. Metab.* 47: 870-876 (1978).
Humphries, et al., *J. Endocrinol.* 102: 57-61 (1984).
Keutmann, et al., *Proc. Natl. Acad. Sci. U.S.A.* 84: 2038-2042 (1987).
Ambesi-Impiombato, et al., *Proc. Natl. Acad. Sci. U.S.A.* 77: 3455-3459 (1980).
Bidey et al., *J. Endocrinol.* 101: 269-276 (1984).
Kasagi et al., *ACTA Endocrinol.* 115: 30-36 (1987).
Morris, et al., *Mayo Clin. Proc.* 63: 707-717 (1988).
Hagenmaier, H. and H. Frank, *Hoppe-Seyler's Z. Physiol. Chem.* 353: S. 1973-1976 (1972).
Kaiser, et al., *Anal. Biochem.* 34: 595-598 (1970).
Lee, C. Y. and R. J. Ryan, *Biochem.* 12: 4609-4615 (1973).
Tramontano, D. and S. H. Ingbar, *Endocrinology* 118: 1945-1951 (1986).
Steiner, et al., *J. Biol. Chem.* 247: 1106-1113 (1972).
Wray, H. L. and A. D. Glinos, *Am. J. Physiol.* 234: C131-C138 (1978).
Klee, G. G. and I. D. Hay, *J. Clin. Endocrinol. Metab.* 64: 461-471 (1987).
Furmaniak, et al., *Acta Endocrinol.*, Suppl. 281: 157-165 (1987).
Furmaniak, et al., *Program of the 62nd Meeting of the American Thyroid Association*, p. T-62 (no. 121) (1987).
Bishop, W. H. and R. J. Ryan, *Biochemistry* 12: 3076-3084 (1973).
Keutmann, et al., *Hoppe-Seyler's Z. Physiol. Chem. Bd.* 355: S. 935-938 (1974).
Ryan, et al., *Recent Prog. Horm. Res.* 43: 383-429 (1987).
Smith et al., *Endocrine Reviews* 9: 106-121 (1988).
Ryan, et al., In *Placental Protein Hormones*, M. Mochizuki and R. Hussa, eds., Elsevier Science Publishers B.V. (Biomedical Division), pp. 111-112 (1988).
Ryan, et al., *FASEB J.* 2: 2661-2669 (1988).

HUMAN BETA TSH 1-112

SYNTHETIC PEPTIDES 1-15   21-35   41-55   61-75   81-95   101-112

SYNTHETIC PEPTIDES DERIVED FROM THE BETA-SUBUNIT OF HUMAN THYROID STIMULATING HORMONE

This invention was made with Government support under grant number HD 9140 by the National Institute of Health and funds from the Mayo Foundation. The Government has certain rights in the invention.

This is a continuation of application Ser. No. 07/403,564, filed Sept. 5, 1989, now abandoned.

BACKGROUND OF THE INVENTION

The gonadotropins, luteinizing hormone (LH) and follicle-stimulating hormone (FSH) of pituitary origin, and chorionic gonadotropin (hCG, eCG) of placental origin, along with thyroid-stimulating hormone or thyrotropin (TSH) constitute a family of glycoprotein hormones. Their isolation, characterization, and biological functions have been the subject of numerous reports. [Licht et al., *Recent Prog. Horm. Res.*, 33:169 (1977); Vaitukaitis et al., *Recent Prog. Horm. Res.*, 32:289 (1976); Ward et al., *Recent Prog. Horm. Res.*, 29:533 (1973); Papkoff et al., *Recent Prog. Horm. Res.*, 29:563 (1973); Canfield et al., *Recent Prog. Horm. Res.*, 27:121 (1971); Pierce et al., *Recent Prog. Horm. Res.*, 27:165 (1971); Ryan et al., *Recent Prog. Horm. Res.*, 26:105 (1970); Pierce in *The Thyroid: A Fundamental and Clinical Text* (Ingbar and Braverman, eds.) pp. 267-271 (5th Ed., J. B. Lippincott, Philadelphia, Pa., 1986)].

Human glycoprotein hormones (TSH, LH, FSH, and hCG) are heterodimers consisting of a hormone specific Betasubunit and a common α-subunit, [Pierce, and Parsons, *Ann. Rev. Biochem.*, 50:465 (1981)]. The intact dimer has been thought to be necessary for full biological activity; however, data on the gonadotropic hormones LH and hCG indicate that both the α and Beta subunits interact with the receptor [Ji and Ji, *Proc. Natl. Acad. Sci. U.S.A.*, 78:5465-5469 (1981); Ascoli and Segaloff, *J. Biol. Chem.*, 261:3807-3815 (1986); Moudgal and Li, *Proc. Natl. Acad. Sci. U.S.A.*, 79:2500-2503 (1982); Grasso and Crisp, *Endocrinology*, 116:319-327 (1985); and Armstrong et al., *Biochemical Actions of Hormones*, 13:91-128 (1986).

To understand the extent to which the particular subunits contribute to the activity of the intact dimer, a need exists to isolate and characterize the subset of peptides within each subunit, which are responsible for the range of biological activities associated with human glycoprotein hormones. Lower molecular weight oligopeptides corresponding to a subunit sequence would be expected to be more readily obtainable, less expensive and exhibit a narrower profile of biological activity than glycoprotein hormones themselves, thus increasing their potential usefulness as therapeutic or diagnostic agents.

One particular human glycoprotein hormone of interest is TSH. TSH exerts its effects by interaction with specific surface receptors found on the plasma membrane of thyroid follicular cells. Although the amino acid sequence of TSH and the structurally similar glycoprotein hormones FSH, LH, and CG have been known for several years (Pierce and Parsons, supra), description of the three-dimensional structure of the hormones and the specific amino acid sequences of the hormone regions responsible for receptor interaction and exertion of biologic activity remains limited.

The structure and function of TSH are of interest in part due to the hormone's role in thyroid disorders. One such disorder is Graves' disease, an autoimmune disease which occurs most often in women and involves overproduction of thyroxin by the thyroid.

Graves' disease is characterized by the presence of immunoglobulins (autoantibodies) that inhibit the binding of TSH to its receptor (thyrotropin binding inhibiting immunoglobulin, TBII) and increase adenylate cyclase activity (thyroid stimulating immunoglobulin, TSI or TRAb) in thyroid follicular cells [Volpe, *The Thyroid: A Fundamental and Clinical Text*, p. 747 (5th ed. 1986)]. The interaction between TSI and TSH receptor has been carefully studied [Smith and Buckland, *Receptors, Antibodies, and Disease CIBA Foundation Symposium*, p. 114 (1982); Fahraeus-Van Ree and Farid, *Clin. Res.*, 31:679A (1983); Davis and Platzer, *Clin. Endocrinol.*, 19:427 (1983)]and current evidence, suggests that the thyrotropin receptor itself is the antigen [Smith and Buckland, supra]. However, the specific binding site remains unknown.

Individuals affected with Graves' disease exhibit exophthalomos, enlarged pulsating thyroid gland, marked acceleration of the heart rate, a tendency to profuse sweats, nervous symptoms, psychic disturbances, emaciation, increased metabolic rate, and pretibial myxedema. Recognized treatment of Graves' disease involves inactivation of the thyroid gland with radioactive iodine, surgical removal of the gland or treatment with certain antithyroid drugs such as propylthiouracil. While present treatments can alleviate the metabolic disorders, they do not prevent continued exophthalomos and pretibial myxedema. The inability to arrest these manifestations may, in part, be due to the failure of current treatments to inhibit binding of long-acting thyroid stimulator (TSI) to cells in the orbit of the eye and skin.

Using a comprehensive synthetic peptide approach, two hormone sites within the common alpha subunit (α26-46 and α81-92) that interact with TSH receptors on human and rat thyroid membranes and with the LH/hCG receptor on rat ovarian membranes have been identified (Morris et al., *Endocrinology*, 123:456-462 (1988); Charlesworth et al., *J. Biol. Chem.*, 262:13409-13416 (1987). These synthetic peptides proved to be inhibitors of TSH bioactivity and the former (α26-46) was shown to inhibit the bioactivity of TSH-receptor auto-antibodies (TRAb or TSI) [Morris et al., *J. Clin. Endocrinol. Metab.*, 67:707-712 (1988)]from patients with Graves' hyperthyroidism. However, the affinity of these synthetic peptides for receptor was quite low ($10^{-4}$ to $10^{-5}$M) suggesting that multiple hormone sites were involved in receptor interaction.

Therefore, there is a need to study and obtain biologically active synthetic beta-subunit peptides of human thyroid stimulating hormone including peptides which can inhibit TSH-mediated cAMP generation; and block the action of TSI.

SUMMARY OF THE INVENTION

The present invention provides polypeptides which represent segments of the beta-subunit of human thyroid stimulating hormone or thyrotropin (TSH). The peptides can be prepared by modified conventional solid phase peptide synthesis. Preferred polypeptide fragments of the present invention correspond substantially to human TSH beta-subunit amino acid residues β1-15, β31-45, β41-55, β71-85, β81-95 and β101-112. These polypeptides inhibit binding of TSH to human thyroid membrane.

The most preferred polypeptides are: (I) Phe-Cys-Ile-Pro-Thr-Glu-Tyr-Thr-Met-His-Ile-Glu-Arg-Arg-Glu; (II) Leu-Ser-Cys-Lys-Cys-Gly-Lys-Cys-Asn-Thr-Asp-Tyr-Ser-Asp-Cys; and (III) Lys-Thr-Asn-Tyr-Cys-Thr-Lys-Pro-Gln-Lys-Ser-Tyr corresponding respectively to isolated β-subunit residues 1-15, 81-95, and 101-112 of human TSH. In the case of (I) and (II), C-terminal amides of these polypeptides are most preferred. These polypeptides were assayed for bioactivity and found to effectively inhibit TSH-mediated cAMP generation, and demonstrate an inhibitory effect on thyroid stimulating immunoglobulin obtained from sera of patients with Graves' disease to stimulate cAMP production by FRTL5 cells.

Since it is expected that further digestion/hydrolysis of polypeptides of the present invention in vitro or in vivo will yield fragments of substantially equivalent bioactivity, such lower molecular weight polypeptides are considered to be within the scope of the present invention, as are mixtures of the polypeptides and functional analogues of the polypeptides.

The polypeptides of the present invention also possess characteristics which can be applied for immunodiagnostic and immunotherapy purposes including competitive and non-competitive assays for thyroid stimulating immunoglobulin. Antibodies raised in response to polypeptides of the present invention can be used as an immunodiagnostic to measure TSab in a patient sample. Also, antibodies raised in response to polypeptides of the present invention can be used therapeutically to neutralize TSab.

BRIEF DESCRIPTION OF THE FIGURES

FIG. 1 is a schematic representation of the strategy used to make synthetic overlapping βTSH peptides. Exact amino acid sequences are shown in Table 1.

FIG. 8 shows peptide 71-85 was effective only at the highest dose of serum tested while peptides 31-45 and 61-75 did not produce a significant effect.

DETAILED DESCRIPTION OF THE INVENTION

Figure 2:
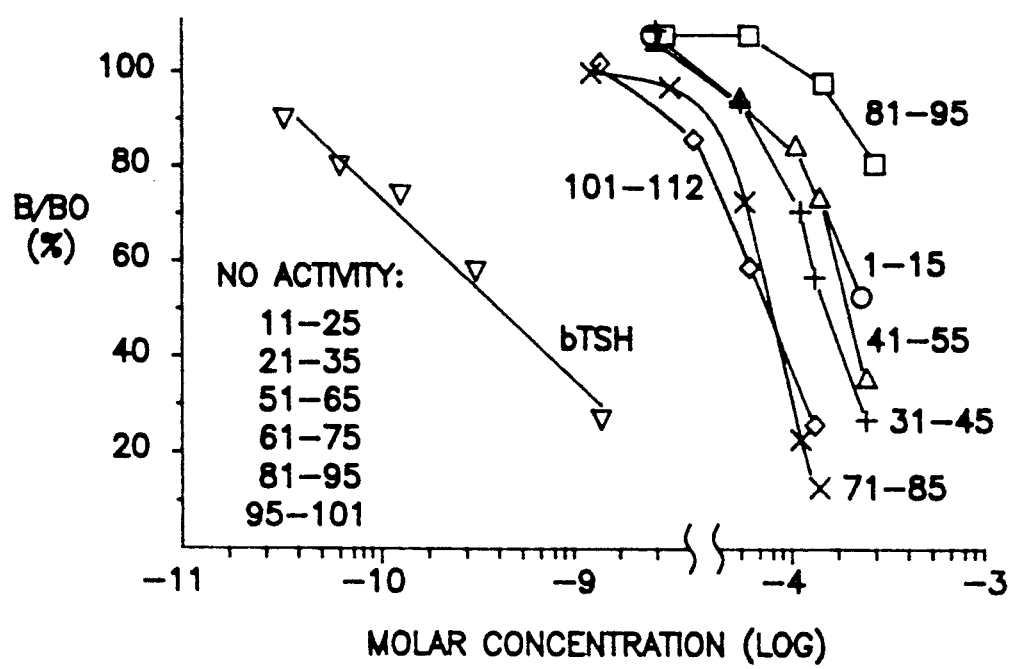
FIG. 2 is a graph depicting inhibition of $^{125}$I-bTSH binding to human thyroid membrane by synthetic β-subunit peptides (human thyroid membrane TSH radioreceptor assay).

We prepared eleven synthetic beta (β)-subunit peptides to study the structure-function relationships of the peptide sequence of the TSH hormone. The receptor binding and biologic activity of these synthetic β-subunit peptides in a human thyroid membrane system and the functional rat thyroid follicular cell line FRTL5 were evaluated. Specifically, the ability of the synthetic peptide fragments of the β-subunit of TSH to interact with the TSH receptor on human thyroid membranes was studied. Selected fragments were evaluated for ability to inhibit TSH-mediated cAMP generation and blocking action of long-acting thyroid stimulator (known as LATS or TSab, thyroid stimulating immunoglobulin).

Synthesis of Polypeptides

Eleven synthetic peptides were assembled representing the entire 112 amino acid sequence of the β-subunit of human TSH. As shown in FIG. 1, an overlapping strategy was employed in order to reduce fragmentation of active regions. Each peptide consisted of 15 amino acid residues and overlapped its adjacent two peptides by 5 residues as shown in Table 1.

The peptides were synthesized by standard solid phase techniques, Steward and Young, *Solid Phase Peptide Synthesis* 2d ed.; Pierce Chemical Co., Rockford Ill., pp. 1-157 (1984); McCormick et al., *J. Immunol.*, 139:2615-2619 (1987), the disclosure of each is incorporated by reference herein using an automated Applied Biosystems 430A peptide synthesizer (Applied Biosystems, Inc., Calif.) on p-methylbenzhydrylamine (copolystyrene) resin. All peptides, except β101-112, which is the C-terminus of the β-subunit, were made as a C terminal amide. Each residue after the first 5 was subjected to two coupling cycles as were all Arg, Asn, and Gln residues to ensure completion of the coupling reaction. Completed peptides were removed from the resin by hydrolysis with liquid hydrogen fluoride at 0° C. for 1.25 hrs., then purified by column chromatography (Sephadex G-25, Pharmacia) in 1M acetic acid and/or reversed phase HPLC. Analytical HPLC using a 220×2.1 mm C-18 column (Brownlee Labs, Santa Clara, Calif.) showed a single major peak for each peptide.

Amino acid composition of the peptides was confirmed by subjecting each to acid hydrolysis followed by precolumn derivatization with phenylisothiocyanate (PITC) as described by Heinrikson and Meredith, *Anal. Biochem.*, 136:65-74 (1984) and as modified as noted in the Waters PICO TAG system (see *Operators Manual*, Waters Co., Milford, Mass.). The derivatized samples were analyzed by HPLC utilizing the Waters PICO TAG column, Beckman 114 pumps, and a Beckman 160 fixed wavelength detector. The data was collected and integrated using an IBM PS/2 model 50Z with the Beckman System Gold chromatography software. The PITC and amino acid standards were purchased from Pierce (Rockford, Ill.). All solvents were HPLC grade. If discrepancies were suspected after composition analysis, the peptide sequence was confirmed by gas-phase microsequencing using an Applied Biosystems 470A protein sequenator employing the OC3PTH programs provided by the manufacturer.

TABLE 1

Amino acid sequence of synthetic human βTSH peptides*

| Position | Sequence |
|---|---|
| 1-15 | Phe—Cys—Ile—Pro—Thr—Glu—Tyr—Thr—Met—His—<u>Ile—Glu—Arg—Arg—Glu</u> |
| 11-25 | <u>Ile—Glu—Arg—Arg—Glu</u>—Cys—Ala—Tyr—Cys—Leu—<u>Thr—Ile—Asn—Thr—Thr</u> |
| 21-35 | <u>Thr—Ile—Asn—Thr—Thr</u>—Ile—Cys—Ala—Gly—Tyr—<u>Cys—Met—Thr—Arg—Asp</u> |
| 31-45 | <u>Cys—Met—Thr—Arg—Asp</u>—Ile—Asn—Gly—Lys—Leu—<u>Phe—Leu—Pro—Lys—Tyr</u> |
| 41-55 | <u>Phe—Leu—Pro—Lys—Tyr</u>—Ala—Leu—Ser—Gln—Asp—<u>Val—Cys—Thr—Tyr—Arg</u> |
| 51-65 | <u>Val—Cys—Thr—Tyr—Arg</u>—Asp—Phe—Ile—Tyr—Arg—<u>Thr—Val—Glu—Ile—Pro</u> |
| 61-75 | <u>Thr—Val—Glu—Ile—Pro</u>—Gly—Cys—Pro—Leu—His—<u>Val—Ala—Pro—Tyr—Phe</u> |
| 71-85 | <u>Val—Ala—Pro—Tyr—Phe</u>—Ser—Tyr—Pro—Val—Ala—<u>Leu—Ser—Cys—Lys—Cys</u> |
| 81-95 | <u>Leu—Ser—Cys—Lys—Cys</u>—Gly—Lys—Cys—Asn—Thr—<u>Asp—Tyr—Ser—Asp—Cys</u> |
| 91-105 | <u>Asp—Tyr—Ser—Asp—Cys</u>—Ile—His—Glu—Ala—Ile—<u>Lys—Thr—Asn—Tyr—Cys</u> |
| 101-112 | <u>Lys—Thr—Asn—Tyr—Cys</u>—Thr—Lys—Pro—Gln—Lys—Ser—Tyr |

*Numbers represent the positions of the residues in intact human bTSH. Underlined regions represent those residues that overlap with the adjacent peptide.

Membrane Preparation

Thyroid tissue from patients with Graves' disease was obtained at surgery and promptly frozen and maintained at −70° C. Crude membrane preparations were prepared from the frozen tissue as previously described, Takahashi et al., *J. Clin. Endocrinol. Metab.*, 47:870-876 (1978), the disclosure of which is incorporated by reference herein. Briefly, the tissue was homogenized with a Polytron homogenizer (Brinkmann Instruments, Westbury, N.Y.), and the 2000×g fraction was collected by centrifugation, washed, and resuspended in 40 mM Tris, 200 mM sucrose, pH 7.4. Membrane preparations were maintained at −70° C. until assay.

Frozen porcine thyroid glands were purchased (Pel-Freez Biologicals, Rogers, Ak.) and prepared using the same procedures as for the human glands.

TSH Radio-Receptor Assays

Highly purified bTSH (30 U/mg, supplied by Dr. J. G. Pierce, formerly of UCLA) was radio-iodinated (Na$^{125}$I, Amersham, Chicago) by a lactoperoxidase technique to a specific activity averaging 40-50 μCi/μg as previously described, Takahashi et al., supra, then purified by Sephadex G-100 chromatography.

The TSH radio-receptor assay (RRA) utilized for the studies has been well described previously; see Takahashi et al., supra and Morris et al., *Endocrinology*, 123:456-462 (1988), the disclosure of which is incorporated by reference herein. Briefly, for either human or porcine thyroid RRA, the incubation mixture consisted of the following: 10 mg equivalents of wet weight (mg eq) crude thyroid membrane preparation, 0.124 ng [$^{125}$I]iodo-bTSH (approximately 20,000 cpm), 0.2% Triton X-100, and the noted amounts of synthetic peptides or unlabeled bTSH in 0.5 ml 40 mM Tris, 0.1% BSA, pH 7.4. Bound label was separated from free after 2 hrs incubation at 25° C. by addition of a 1 ml 30% polyethylene glycol (PEG, Baker, Phillipsburg, N.J.) 6000 in 1M NaCl and centrifugation. The resulting pellet was counted in a gamma counter. Non-specific binding was determined by addition of a 100 mU/ml crude bTSH (Sigma, St. Louis).

EGF Radio-Receptor Assays

The EGF RRA was a modification of that described by Humphries et al., *J. Endocrinol.*, 102:857-61 (1984), the disclosure of which is incorporated by reference herein. Purified murine EGF (a gift of Dr. N. S. Jiang, Mayo Clinic) was radio-iodinated by a chloramine-T technique to a specific activity of 65 μCi/μg. The incubation mixture consisted of 40 mg eq crude thyroid membrane, 0.5 ng [$^{125}$I]iodo-EGF, and the indicated concentrations of unlabeled EGF or synthetic peptides in 0.5 ml phosphate buffered saline plus 5 mM MgCl$_2$, 1 mM CaCl$_2$, 0.1% BSA, pH 7.4. Non-specific binding was determined by addition of 0.5 μg unlabeled EGF. Bound was separated from free by precipitation with PEG and centrifugation as above.

Inhibition of $^{125}$I-bTSH Binding to Thyroid Membrane Preparations by Synthetic βTSH Peptides

Human Thyroid RRA

FIG. 2 and Table 2 show the results of the human thyroid radio-receptor assays.

Four regions of the human βTSH subunit were represented by five active peptides. The highest activity was found in the peptide representing the -COOH terminus of the subunit β101-102 which inhibited [$^{125}$I]iodo-bTSH binding with an EC$_{50}$ of 80±9 μM. Two peptides representing the region of the subunit between residues 71 through 95 were also active, β71-85 with an EC$_{50}$ of 104±15 μM and β81-95 with an EC$_{50}$ of 1196±139 μM. Because these two peptides overlap each other and because both show activity, the active region is believed to involve the region of overlap (residues 81-85), and, perhaps, extend somewhat towards the amino end of the region in order to explain the higher activity of the more proximal peptide β71-85.

Activity was also observed in the two peptides β31-45 and β41-55. However, these βTSH sequences were significantly less potent in inhibition of TSH binding (186±25 and 242±58 μM for β31-45 and β41-55, respectively) than was previously reported for the βLH sequence in hCG/LH RRA (20.3) μM) by Keutmann et al., *Proc. Natl. Acad. Sci. U.S.A.*, 84:2038-2042 (1987). This suggests that this region may be less important for TSH binding than it is for the gonadotropins.

Finally, activity was noted in the peptide representing the amino terminus of βTSH, β1-15 which inhibited binding of the label with an EC$_{50}$ of 331±45 μM.

The peptides representing the remainder of the βTSH sequence possessed no ability to inhibit hormone/receptor interaction, indicating that the effect of the active peptides is sequence specific.

Porcine Thyroid RRA

Figure 3:
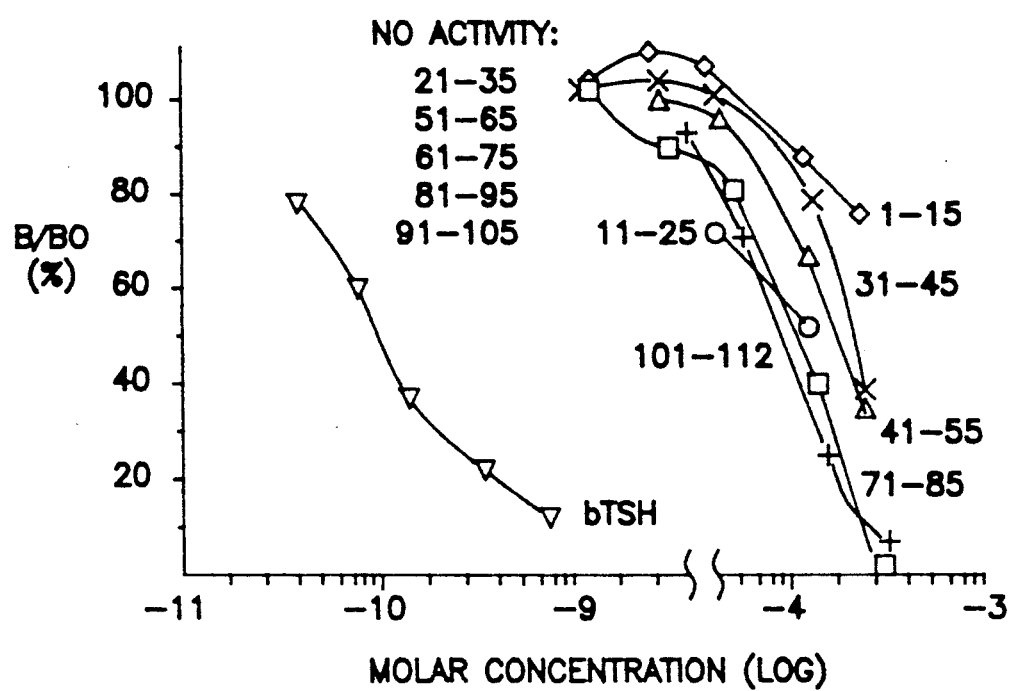
FIG. 3 is a graph depicting inhibition of $^{125}$I-bTSH binding to porcine thyroid membrane by synthetic β-subunit peptides (porcine thyroid membrane TSH radio-receptor assay).

FIG. 3 shows the activity of the synthetic βTSH peptides in the TSH RRA using porcine thyroid membranes. Four regions of activity similar to those found in the human thyroid RRA were found. Again β101-112 and β71-85 were most potent showing EC$_{50}$ values of 106±8.7 and 137±14 μM respectively. The intercysteine loop region was represented by the peptides β31-45 and β41-55 (EC$_{50}$ of 200±36 and 216±18 μM respectively). The amino terminal peptide β1-15 was also active with an EC$_{50}$ of 1158±431 μM.

The peptide β11-25 showed differential activity in the two TSH RRA's. Although it was inactive in the human membrane assay, it showed significant inhibitory activity in the porcine assay with an EC$_{50}$ of 186±28 βM. This may represent a region of βTSH that is recognized by the porcine TSH receptor but is not recognized by the human receptor. This may also, at least in part, explain the higher binding activity of unlabeled TSH in the porcine RRA versus the human membrane assay (Table 2).

As noted in FIG. 3, the remaining peptides had no activity, again demonstrating the sequence specificity of the effect.

TABLE 2

Inhibition of TSH Binding to Thyroid Membrane Homogenates by Synthetic βTSH Peptides

| Peptide | Human EC$_{50}$ μM | Porcine EC$_{50}$ μM |
|---|---|---|
| β1-15 | 331 ± 45 | 1158 ± 431 |
| β11-25 | >1000 | 186 ± 28 |
| β21-35 | >1000 | >1000 |
| β31-45 | 186 ± 25 | 200 ± 36 |
| β41-55 | 242 ± 58 | 216 ± 18 |
| β51-65 | >1000 | >1000 |
| β61-75 | >1000 | >1000 |
| β71-85 | 104 ± 15 | 137 ± 14 |
| β81-95 | 1196 ± 139 | >1000 |
| β91-105 | >1000 | >1000 |
| β101-112 | 80 ± 9 | 106 ± 8.7 |
| bTSH (pM) | 540 ± 0.04 | 114 ± 0.01 |

Values represent mean ± se of at least 3 separate assays.
EC$_{50}$ represents the concentration of peptide or hormone needed to inhibit binding of $^{125}$I-bTSH to the respective membrane fraction by 50%.

Epidermal growth factor RRA

Figure 4:
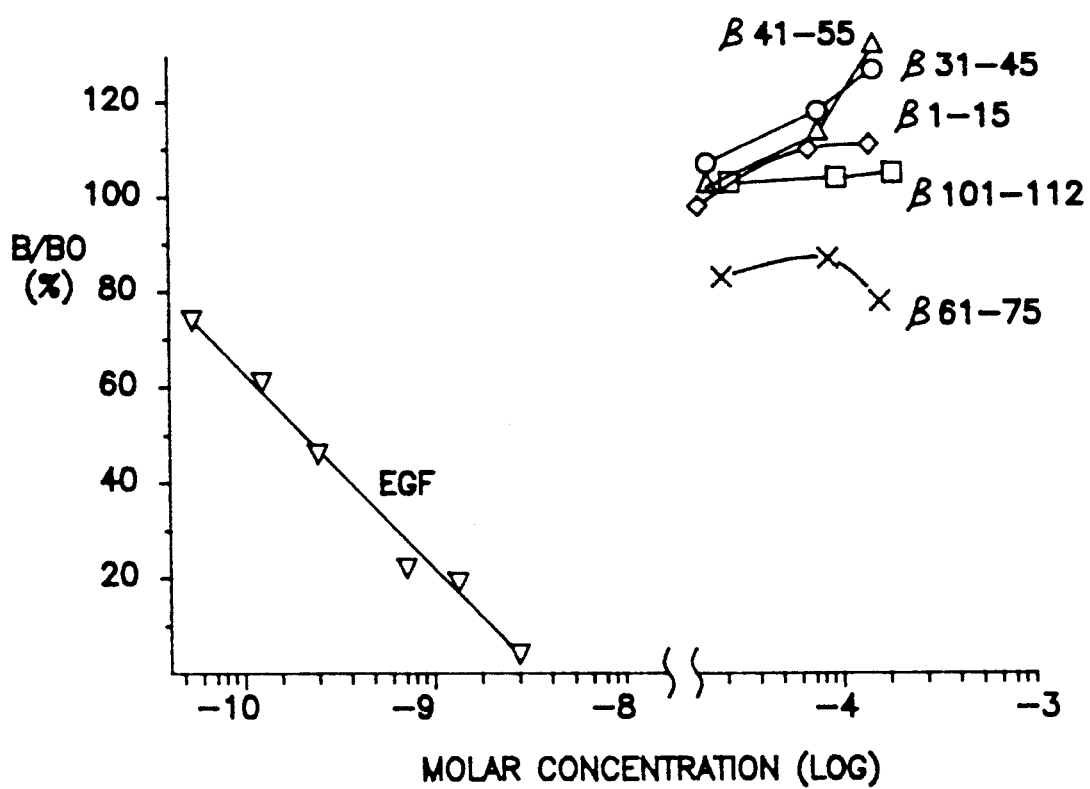
FIG. 4 is a graph depicting lack of inhibition of $^{125}$I-bTSH binding to porcine thyroid membrane by synthetic β-subunit peptides (porcine thyroid membrane epidermal growth factor radio-receptor assay.)

Studies utilizing the EGF RRA were designed to determine the specificity of the synthetic βTSH peptides for interaction with the TSH specific receptor, and to exclude a nonspecific membrane effect as the cause of the activity. As noted in FIG. 4, high affinity binding of EGF could be demonstrated to the porcine thyroid membrane preparations as has been previously noted by Humphries et al., supra. The EC$_{50}$ of unlabeled EGF in this assay (252 pM) is quite similar to that of unlabeled TSH in the TSH RRA using the same porcine membranes (114 pM). As shown in the figure, none of the active synthetic βTSH peptides significantly inhibited binding of [$^{125}$I]iodo-EGF to its thyroid membrane receptor.

Cell Cultures

FRTL$_5$ cells were cultured in Hams F-12 medium supplemented with 5% calf serum and a preparation containing 6 hormones (6H), including 10 mU/ml bTSH (Sigma, St. Louis, Mo.), as previously described. Ambesi-Impiombato et al., *Proc. Natl. Acad. Sci. U.S.A.*, 77:3455 (1980), the disclosure of which is incorporated by reference herein. The cells were enzymatically removed from flasks and plated in 24 well plates containing 6H at a density of 150,000 cells per well. After 4 days, the cells were washed and the media replaced with media containing insulin only (1H). All subsequent assays were performed on cells deprived of TSH for 5-7 days.

TSH Bioassay

The TSH bioassay was a modification of assays previously described by Bidey et al., *J. Endocrinol.*, 101:269 (1984); and Kasagi et al., *ACTA Endocrinol.*, 115:30 (1987). FRTL$_5$ cells were washed with NaCl-free Hanks balanced salt solution (NaCl-free HBSS) pH 7.3. The cells were then exposed to purified bovine TSH (bTSH) (a gift from Dr. John Pierce, formerly of UCLA) in the presence and absence of specific β-subunit peptides in NaCl-free HBSS with 0.5 mM isobutylmethylxanthine (IBMX, Sigma, St. Louis, Mo.) and 0.5% BSA (Sigma). The total volume in each well was 275 μl. In stimulation assays, only the β-subunit peptides were added. For inhibition assays, two different concentrations of the β-subunit peptides were added to culture wells in duplicate with 200 mU/l of purified bTSH. The plates were incubated for 2 hours at 37° C. in 5% CO$_2$. The media was removed from the cells and a portion diluted 1:50 in 0.05M NaOAc buffer, pH 6.2. A 25 μl aliquot of this was used in a cAMP RIA. Basal cAMP levels were determined in the absence of the TSH or β-subunit peptides. In inhibition assays, the percent inhibition was calculated as noted below (see Morris et al., (1988) supra):

$$\% \text{ inhibition} = 100 \times 1 - \frac{(\text{pmol cAMP sample} - \text{pmol basal})}{(\text{pmol cAMP TSH} - \text{pmol basal})}$$

TSab serum samples

Serum samples from 15 patients with elevated TSab levels were selected from the clinical chemistry laboratory. The TSab values, expressed as an index, $$\frac{\text{pmol cAMP sample}}{\text{pmol cAMP basal}} \text{,[see Morris et al., May Clin. Proc.,}$$

63:707 (1988)]ranged from 10-20 with an average of 13.8±3.3. Normal serum has an index of less than 1.3.

TSab Bioassay

The bioassay described by Kasagi et al., supra, with modifications as previously noted above, was used. The immunoglobulins were precipitated from 2 ml of TSab-containing serum with 6 ml of polyethylene glycol 6,000 (Baker; Phillipsburg, N.J.), centrifuged at 3,000×g for 20 minutes, and resuspended in 4 ml of NaCl-free HBSS with 0.5 mM IBMX and 0.5% BSA. The plated cells were washed with NaCl-free HBSS and the crude immunoglobulin extract, mixed with various concentrations of β-subunit peptides, was added in duplicate to the wells (total volume 200 μl/well). The cells were incubated for 2 hours at 37° C. and 5% $CO_2$. The samples were then removed from the cells and a portion diluted 1:50 in NaOAc buffer, pH 6.2. A 25 μl aliquot of this was then used in a cAMP RIA as described above. The basal cAMP levels were determined for each plate of cells in the absence of immunoglobulin extract and β-peptides. A maximal cAMP level was attained by stimulating the cells with the immunoglobulin extract only. The percent increase in cAMP levels above basal was calculated as:

$$\% \text{ increase over basal} = \frac{\text{pmol cAMP sample} - \text{pmol cAMP basal}}{\text{pmol cAMP basal}} \times 100$$

as previously described (see Morris et al., supra). The percent inhibition of cAMP production by the β-subunit peptides was calculated as described above for TSH-stimulated cells, substituting pmol cAMP crude immunoglobulin for pmol cAMP TSH.

Statistical Analysis

Inhibition of TSab activity was tested by comparing the replicates of cAMP levels generated in the presence of peptide to those generated by TSab alone using Student's T test for unpaired samples. Mean inhibition by the various doses of synthetic peptide for the patient group was tested by comparison with maximum cAMP response within each patient sample using the T test for paired samples.

Stimulation of cAMP by TSH and β-Subunit Peptides

Each β-subunit peptide was tested in the bioassay at three concentrations (the two concentrations listed in Table 3, plus a third 2-fold higher than the highest noted) to determine their ability to stimulate cAMP generation. Each culture was incubated with 0.5 mM IBMX to prevent degradation of the generated cAMP. None of the β-subunit peptides stimulated an increase in cAMP level at any of the concentrations tested.

Inhibition of TSH-Stimulated cAMP Generation by β-Subunit Peptides

Figure 5:
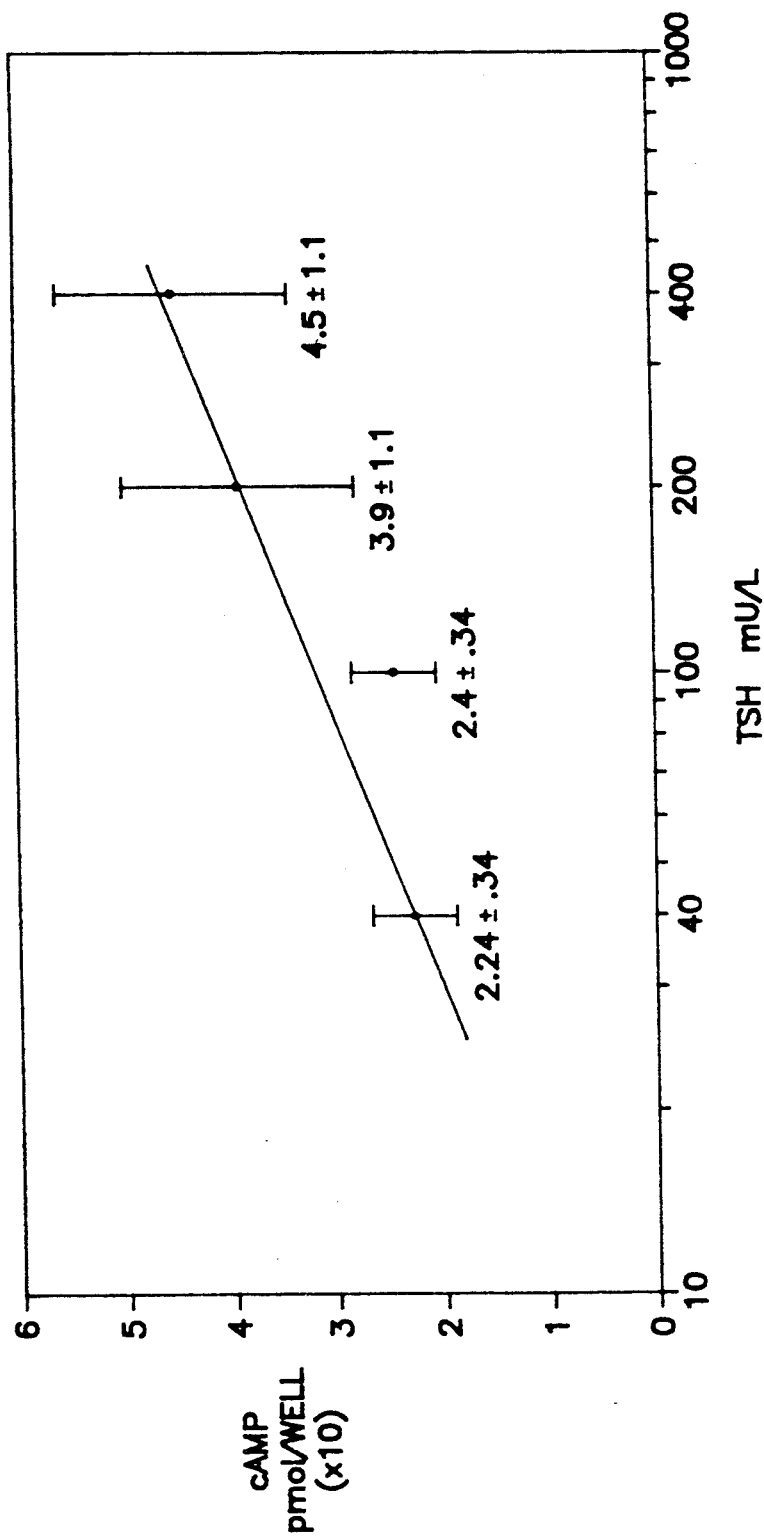
FIG. 5 is a graph depicting the standard curve for TSH stimulated cAMP production in FRTL5 cells.
Figure 6:
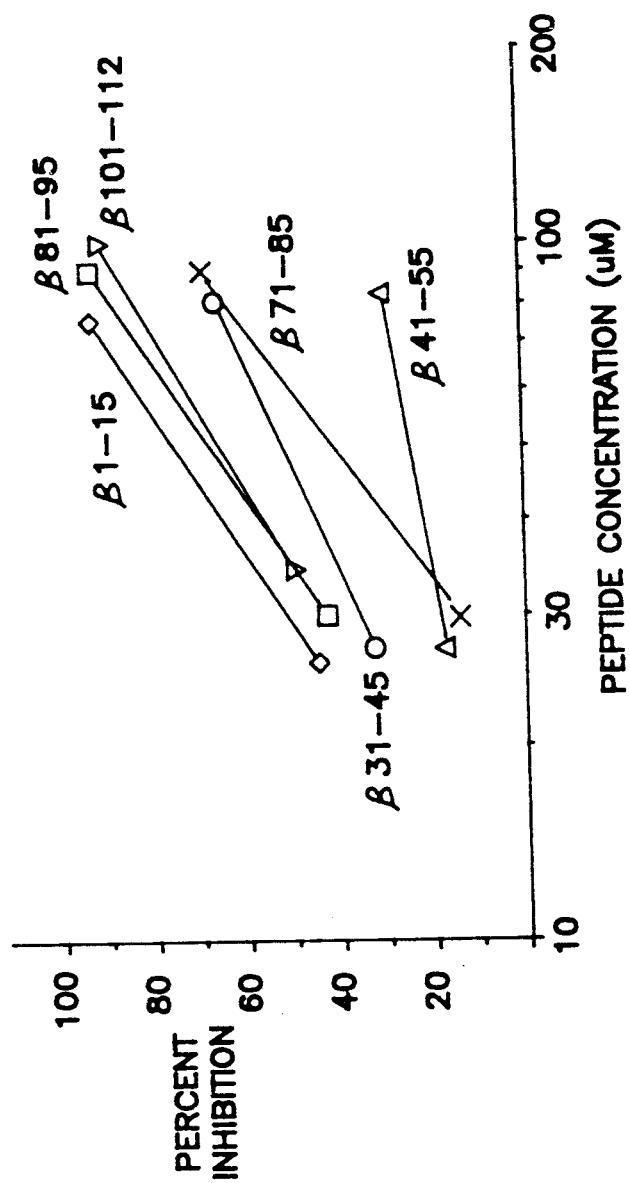
FIG. 6 is a graph depicting inhibition of TSH-mediated cAMP generation in FRTL5 cells by synthetic human TSH β-subunit peptides.
Figure 7B:
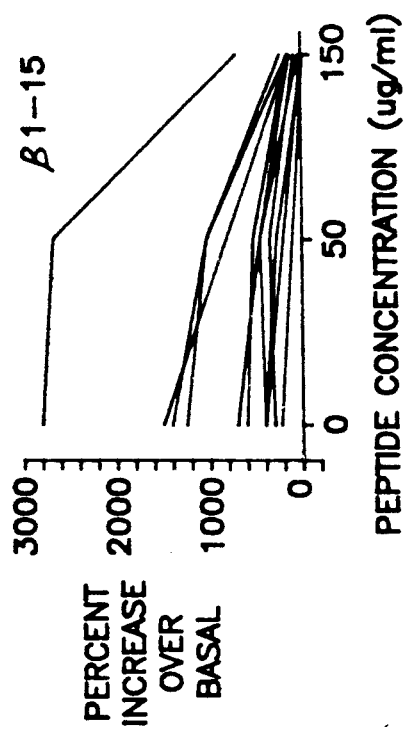
FIG. 7 is a graph depicting inhibition of thyroid stimulating immunoglobulin mediated cAMP generation in FRTL5 cells by synthetic β-subunit peptides 102-112, 1-15, 81-95 and 91-105. Each line represents a serum sample from a different patient with Graves' disease.
Figure 7D:
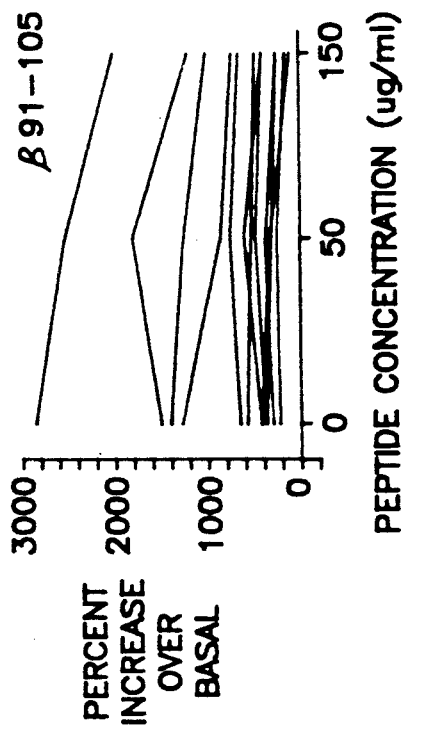
Figure 7A:
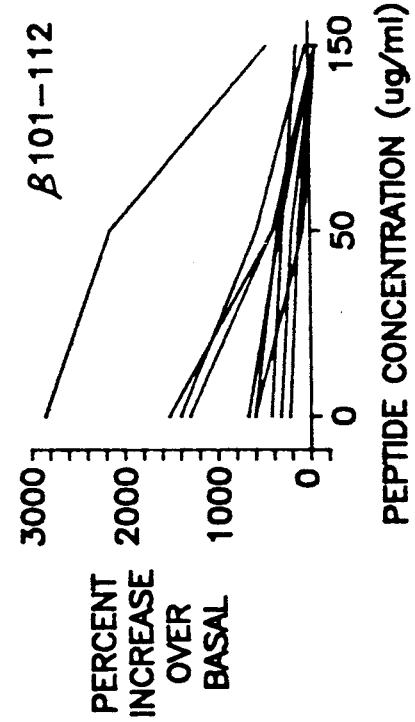
Figure 7C:
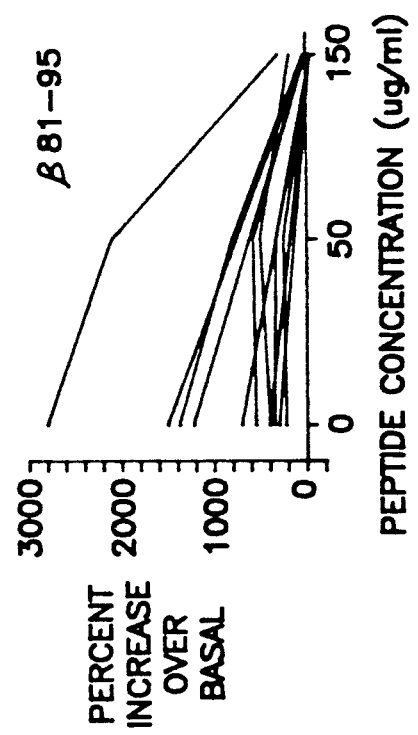

The addition of increasing concentrations of bTSH to $FRTL_5$ cell cultures resulted in a linear increase in cAMP production (FIG. 5). The maximum amount of bTSH used, 400 mU/l ($5.0\times10^{-10}$M), resulted in a 4.5±2.1-fold increase in cAMP levels over the basal level at 2 hours. This increase in cAMP was inhibited by several of the individual β-subunit peptides as summarized in Table 3 and FIG. 6. The three most potent inhibitors of TSH-mediated cAMP generation were β1-15 (90.7±9.1% inhibition at a concentration of 78 μM), β81-95 (91.0±7.0% inhibition at 92 μM) and a β101-112 (89.3±8.5% inhibition at 104±μM). The concentrations of peptide required for 50% inhibition ($IC_{50}$) were 32±6.2 μM, 38.3±7.6 μM and 36.7±21.8 μM for β1-15, β81-95, and β101-112, respectively. Two additional peptides, β31-45 and β71-85, also demonstrated some inhibitory activity (62.7±3.5% inhibition at 84 μM and 55.0±11.3% inhibition at 91 μM, respectively) but were less potent, with $IC_{50}$ values of 53.2±8.8 μM and 70.1±2.9 μM. The remaining seven peptides possessed little or no ability to inhibit TSH activity. The inhibitory activity of β41-55 plotted in FIG. 6 was illustrative of these inactive peptides.

TABLE 3

Inhibition of TSH-mediated cAMP generation in $FRTL_5$ cells by synthetic human TSH β-subunit peptides.

| Ligand | Conc. (μM) | n | % Inhibition (mean ± SD) | $IC_{50}$ (μM) |
|---|---|---|---|---|
| β1-15 | 26 | 3 | 41.3 ± 8.5 | 32.0 ± 6.2 |
|  | 78 | 3 | 90.7 ± 9.1 |  |
| β11-25 | 28 | 3 | 0 | >1000 |
|  | 84 | 2 | 21.9 ± 11.3 |  |
| β21-35 | 30 | 3 | 19.7 ± 17.9 | >500 |
|  | 90 | 3 | 29.0 ± 13.7 |  |
| β31-45 | 29 | 3 | 31.0 ± 7.9 | 53.2 ± 8.8 |
|  | 84 | 3 | 6.27 ± 3.5 |  |
| β41-55 | 28 | 2 | 18.6 ± 0.6 | >500 |
|  | 83 | 2 | 29.0 ± 28.0 |  |
| β51-65 | 27 | 2 | 0 | >1000 |
|  | 80 | 2 | 14.1 ± 9.8 |  |
| β61-75 | 31 | 2 | 0 | 332.0 ± 0.0 |
|  | 91 | 2 | 23.0 ± 0.0 |  |
| β71-85 | 30 | 3 | 12.7 ± 21.9 | 70.1 ± 2.9 |
|  | 91 | 3 | 65.7 ± 20.1 |  |
| β81-95 | 31 | 3 | 39.3 ± 10.1 | 38.3 ± 7.6 |
|  | 92 | 3 | 91.0 ± 7.0 |  |
| β91-105 | 28 | 3 | 8.0 ± 11.4 | >500 |
|  | 85 | 3 | 22.0 ± 3.6 |  |
| β101-112 | 35 | 3 | 45.3 ± 24.9 | 36.7 ± 21.8 |
|  | 104 | 3 | 89.3 ± 8.5 |  |

Inhibition of TSab-Stimulated cAMP Generation by β-Subunit Peptides

Serum samples containing variable levels of TSab activity stimulated cAMP generation in $FRTL_5$ cells by 592±347% (mean±SD) over basal levels. TSab-stimulated cAMP production was inhibited by four β-subunit peptides (Table 4). The most active peptides were β1-15, β81-95 and β101-112, all of which significantly inhibited cAMP production (p<0.01) at concentrations of 50 and 150 μg/ml. The peptide β71-85 showed significant inhibition only at the highest concentration. Mean inhibition achieved by peptides at a concentration of 150 μg/ml was 96.3±18.7%, 105±10.0%, 106±10.1% and 40.0±26.0% for β1-15, β81-95, β101-112 and β71-85, respectively. Two β-subunit peptides which were included as controls, β91-105 and β61-75, did not inhibit TSab activity. The peptide β31-45, which inhibited TSH-mediated cAMP production as noted above, did not significantly inhibit TSab activity at either concentration.

Figure 8C:
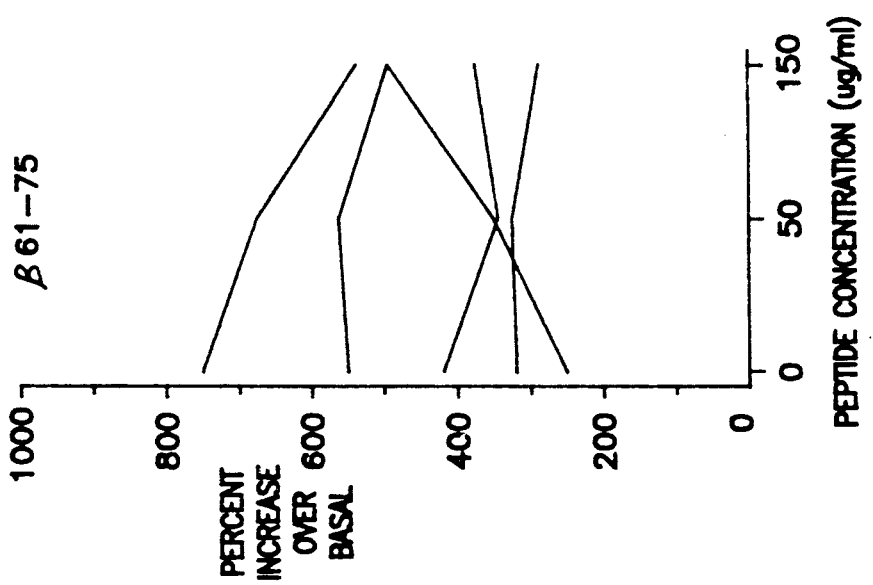
FIG. 8 is a graph depicting inhibition of thyroid stimulating immunoglobulin stimulated-mediated cAMP generation by synthetic β-subunit peptides 71-85, 31-45 and 61-75.
Figure 8B:
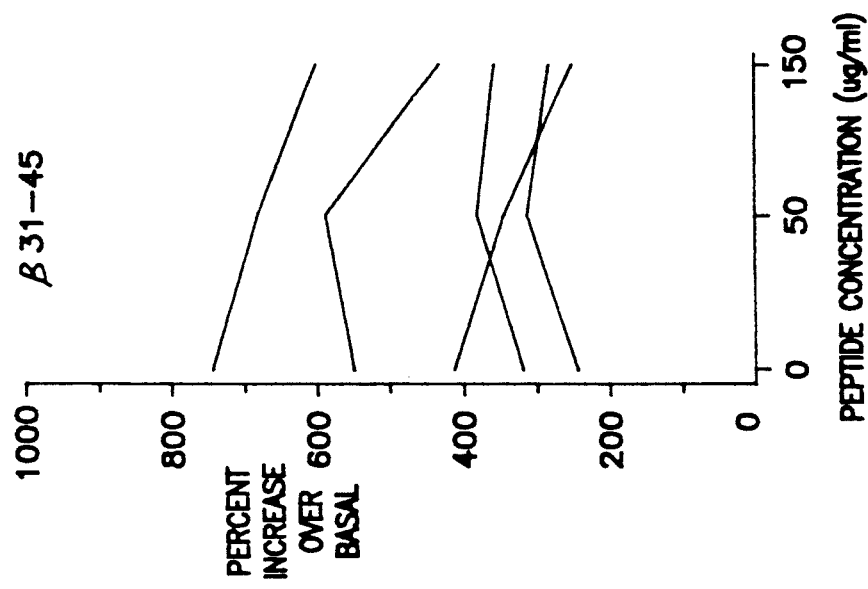
Figure 8A:
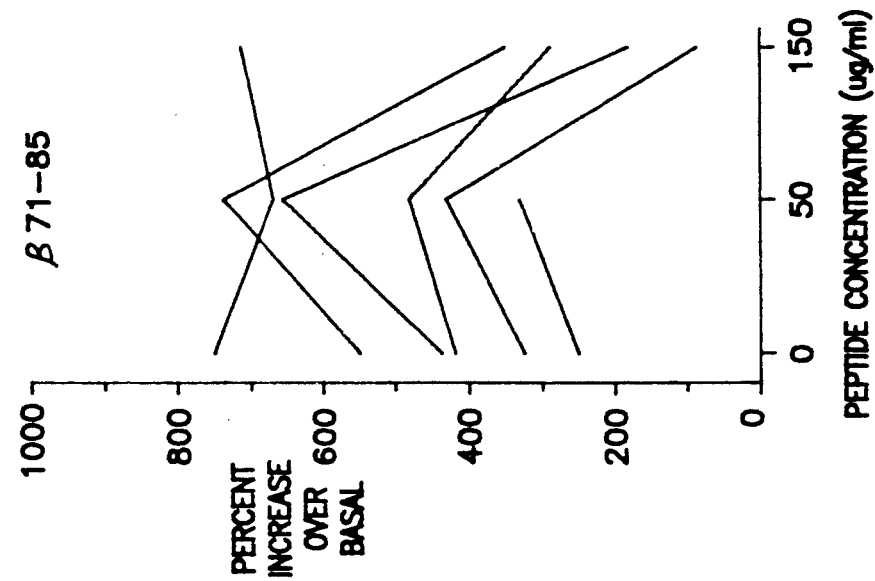

TSab-stimulated cAMP was significantly inhibited (p<0.05) by β1-15 (150 μg/ml) in 12/12 serum samples tested, by β81-95 in 10/11 samples, and by β101-112 in 10/11 samples tested (FIG. 7). Although β71-85 showed significant inhibition at 150 μg/ml, it was only able to significantly inhibit TSab-stimulated cAMP generation in 1/5 serum samples tested (FIG. 8). The inactive peptides, β91-105, β31-45 and β61-75 were able to significantly inhibit TSab-stimulated-mediated cAMP generation in only 1/12, 1/5 and 1/5 serum samples tested, respectively (FIG. 8).

TABLE 4

Inhibition of TSab-Stimulated cAMP Generation by TSH β-Subunit Peptides

| Peptide |  | n | Mean Inhibition % ± SD |
|---|---|---|---|
| β1-15 | 50 μg/ml | 12 | 28.7 ± 24.7* |
|  | 150 μg/ml | 12 | 96.3 ± 18.7* |

TABLE 4-continued

Inhibition of TSab-Stimulated cAMP Generation by TSH β-Subunit Peptides

| Peptide | | n | Mean Inhibition % ± SD |
|---|---|---|---|
| β81-95 | 50 μg/ml | 12 | 38.5 ± 35.3* |
| | 150 μg/ml | 11 | 105.0 ± 10.0* |
| β101-112 | 50 μg/ml | 12 | 55.0 ± 24.0* |
| | 150 μg/ml | 11 | 106.0 ± 10.1* |
| β91-105 | 50 μg/ml | 12 | 9.29 ± 14.6 |
| | 150 μg/ml | 123 | 1.10 ± 32.2 |
| β71-85 | 50 μg/ml | 6 | 1.6 ± 1.4 |
| | 150 μg/ml | 6 | 40.0 ± 26.0* |
| β31-45 | 50 μg/ml | 5 | 4.8 ± 7.4 |
| | 150 μg/ml | 5 | 16.1 ± 16.8 |
| β61-75 | 50 μg/ml | 5 | 5.92 ± 8.54 |
| | 150 μg/ml | 5 | 11.70 ± 9.70 |

*p ≤ 0.01 vs maximal response

In accordance with the present invention, the data herein indicates that synthetic peptides corresponding to regions of the β-subunit of human thyroid stimulating hormone, have broad utility. These peptides exhibit important biological activity including inhibition of TSH binding to human thyroid membrane; inhibition of TSH stimulation of cAMP production; and inhibition of the stimulatory effect of TSab contained in serum from patients with elevated TSab in an in vitro bioassay (cAMP generation by FRTL5 cells). Therefore, it is believed these synthetic peptides can be useful as therapeutic or diagnostic agents. For example, it is believed that one of skill in the art will recognize that the peptides of the present invention, and particularly β1-15, β101-112, and β81-95 mimic regions of the thyroid stimulating autoantibodies (TSI) that interact with the TSH receptor. It is also believed that one of skill in the art can produce antibodies made to these peptides which will bind the thyroid stimulating autoantibodies. These antibodies to the peptides could, therefore, be used to measure TSI. They could also be used therapeutically. For example, the antipeptide antibodies could be attached to a solid phase support and be used in a plasmaphoresis system to remove TSI from the circulation of patients with Graves' disease. A method for measuring thyroid stimulating immunoglobulin in sera of patients with thyroid disorders would involve contacting a sample of said serum or plasma with an antibody to a polypeptide corresponding to a βsubunit region of human thyroid stimulating hormone (TSH) which inhibits TSH-mediated cAMP generation and stimulatory ability of thyroid stimulating immunoglobulin; and measuring bound or unbound antibody or TSI in order to quantitate the amount of TSI.

It is further recognized that the practical usefulness of the peptides derived from regions of the β-subunit (such as 101-112, 81-95, and 1-15) can be enhanced by modifications that would (1) inhibit proteolytic cleavages and thus prolong their circulatory half-life, (2) increase immunogenicity, and/or (3) increase intrinsic biological activity. Therefore, peptides of the present invention, envision synthetic peptides corresponding to specific β-subunit such as 101-112, 81-95, and 1-15, and analogous peptides that have been modified by any of the following:

(1) deletion of amino acids at particular locations in the sequence(s);

(2) substitution of residues in the sequence(s) with any of the 20 common L-amino acids or their natural metabolic derivatives (i.e., hydroxyproline, hydroxylysine, etc.) or their D-amino acid counterparts, either L or D forms of amino acids that occur naturally but are not found in proteins or peptides (ornithine and citrulline, for example) or synthetic amino acids of either L or D form such as norleucine and norvaline;

(3) chemical modifications which sulfonate, phosphorylate, halogenate, nitrate, nitrosylate or oxidize susceptible residues in the sequence;

(4) chemical modifications which acylate or alkylate susceptible residues including the N-terminus (such modifying agents might include adjuvants such as N-acetylmuramic acid);

(5) chemical modifications which leave the C-terminus as a free carboxyl group and esterifications of this free carboxyl group; and (6) any chemical modification of susceptible residues such as the N-terminus, the C-terminus, cysteine, methionine, tyrosine, arginine, lysine, serine and threonine.

What is claimed is:

1. A polypeptide of the formula:

NH2-Lys-THr-Asn-Tyr-Cys-Thr-Lys-Pro-Gln-Lys-Ser-Tyr-COOH.

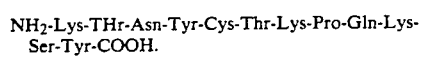

UNITED STATES PATENT AND TRADEMARK OFFICE
CERTIFICATE OF CORRECTION

PATENT NO. : 5,196,513
DATED : March 23, 1993
INVENTOR(S) : Robert J. Ryan et al.

It is certified that error appears in the above-identified patent and that said Letters Patent is hereby corrected as shown below:

At column 7, line 31, for "$\beta M$" read --$\mu M$--

At column 8, line 57, for "May" read --Mayo--

At column 10, line 15, for "6.27" read --62.7--

At column 10, line 38, for "(p < 0.01)" read --(p ≤ 0.01)--

At column 11, line 17, for "*p ≦ 0.01" read --*p ≤ 0.01--

At column 12, line 44, for "THr" read --Thr--

Signed and Sealed this

Twenty-sixth Day of April, 1994

Attest:

BRUCE LEHMAN

Attesting Officer    Commissioner of Patents and Trademarks